United States Patent [19]
Yuan et al.

[11] Patent Number: 5,522,902
[45] Date of Patent: Jun. 4, 1996

[54] FEMORAL COMPONENT USED IN ARTIFICIAL KNEE JOINT

[76] Inventors: Hansen A. Yuan, 5066 Pine Valley Dr., Fayetteville, N.Y. 13066; David G. Murray, 5 Quaker Hill Rd., Syracuse, N.Y. 13224; Chih-I Lin, 14292 Spring Vista La., Chino Hills, Calif. 91709

[21] Appl. No.: 207,613

[22] Filed: Mar. 9, 1994

[51] Int. Cl.⁶ ..................................................... A61F 2/38
[52] U.S. Cl. .............................................. 623/20; 623/18
[58] Field of Search ................................. 623/20, 16, 18, 623/23, 22

[56] References Cited

U.S. PATENT DOCUMENTS

| | | | |
|---|---|---|---|
| 4,565,193 | 1/1986 | Streli | 606/69 |
| 4,578,081 | 8/1986 | Harder et al. | 623/20 |
| 5,006,120 | 4/1991 | Carter | 606/69 |
| 5,282,867 | 2/1994 | Mikhail | 623/20 |
| 5,330,531 | 7/1994 | Capanna | 623/18 |

FOREIGN PATENT DOCUMENTS

| | | | |
|---|---|---|---|
| 0567424 | 10/1993 | European Pat. Off. | 623/17 |
| 2578162 | 9/1986 | France | 623/22 |
| 2614524 | 11/1988 | France | 623/23 |

OTHER PUBLICATIONS

Stemmed Femoral and Patellar Components, p. 16C, catalog of Howmedica, Inc., U.S.A.

Femoral and Patella Components, p. 22C, catalog of Howmedica, Inc., U.S.A.

*Primary Examiner*—David Isabella
*Attorney, Agent, or Firm*—Bacon & Thomas

[57] ABSTRACT

A femoral component used in an artificial knee joint has an integral body provided with a lateral condyle protecting top, a medial condyle protecting top, and a condyle groove protecting edge. The lateral condyle protecting top and/or the medial condyle protecting top are provided respectively with at least one retaining slot or hooking eye in the outer side thereof. The retaining slot or hooking eye serves to enable the femoral component used in the artificial knee joint to work in combination with a femoral hipbone rehabilitating device, such as a bone plate.

2 Claims, 3 Drawing Sheets

FEMORAL COMPONENT USED IN ARTIFICIAL KNEE JOINT

FIELD OF THE INVENTION

The present invention relates generally to an artificial knee joint, and more particularly to a femoral component of an artificial knee joint.

BACKGROUND OF THE INVENTION

The femoral component of the conventional artificial knee joint, such as the one made by Howmedica Corporation of the United States, is not provided with a coupling means capable of combining the femoral component with another fixation device. Such a femoral component as proposed by the prior art is defective in design in that it is incapable of cooperating with a conventional bone plate to fix the femur that is deformed or injured after the femoral component of the artificial knee joint has been implanted to fix the deformed or injured knee joint. In other words, only a few bone screws can be fastened onto a fractured femur adjacent to the femoral component of the artificial knee joint, thereby resulting in a poor fixing effect. Furthermore, the femoral component of the conventional artificial knee joint is devoid of a coupling means and is therefore unable to unite with the bone plate having a compression hole. This means that the femoral component of the artificial knee joint can not be used as a point of application to force the fractured femur to close the fracture by means of the compression hole of the bone plate.

SUMMARY OF THE INVENTION

It is therefore the primary objective of the present invention to provide femoral component used in an artificial knee joint, which has a coupling means capable of fastening the femoral component with a coupling element of a bone plate for rehabilitating a deformed or injured femoral hipbone.

It is another objective of the present invention to provide an artificial knee joint having such a femoral component.

In keeping with the principle of the present invention, the foregoing objectives of the present invention are attained by a femoral component used in an artificial knee joint, which is integrally made up of a lateral condyle protecting top, a medial condyle protecting top, and a condyle protecting edge connecting the lateral condyle protecting top and the medial condyle protecting top. The lateral condyle protecting top and the medial condyle protecting top are provided respectively with a posterio femoral condyle protecting edge. The femoral component of the present invention is characterized in that the lateral condyle protecting top and/or the medial condyle protecting top are provided respectively at the outer side thereof with a coupling means.

The femoral component of the present invention is similar in construction to that of the femoral component used in the artificial knee joint of the prior art, such as the femoral component of the artificial knee joint made by Howmedica Corporation of the United States. The femoral component of the present invention is made of the same material as that of the artificial knee joint of the prior art.

The coupling means of the femoral component of the present invention is intended to couple with the coupling elements of a femoral hipbone rehabilitating bone plate. The coupling method of the present invention is similar to any coupling method of the prior art, such as a hooking method.

The coupling means of the femoral component of the present invention constitutes, for example, a retaining slot. Preferably, the femoral component of the present invention is provided with one to two retaining slots, which are respectively engageable with hooked coupling elements of the femoral hipbone rehabilitating bone plate. The hooked coupling elements are equal in number to the retaining slots. The present invention may be provided with the hooked coupling elements engageable with the retaining slots of the femoral hipbone rehabilitating bone plate. The present invention may be alternatively provided with another type of the coupling means, such as a threaded hole engageable with a screw serving as a coupling element of the femoral hipbone rehabilitating bone plate. However, the hooking method is recommended.

The foregoing objectives, structures, functions and features of the present invention will be more readily understood upon a thoughtful deliberation of the following detailed description of the present invention in conjunction with the drawings provided herewith.

DETAILED DESCRIPTION OF THE INVENTION

Figure 1:
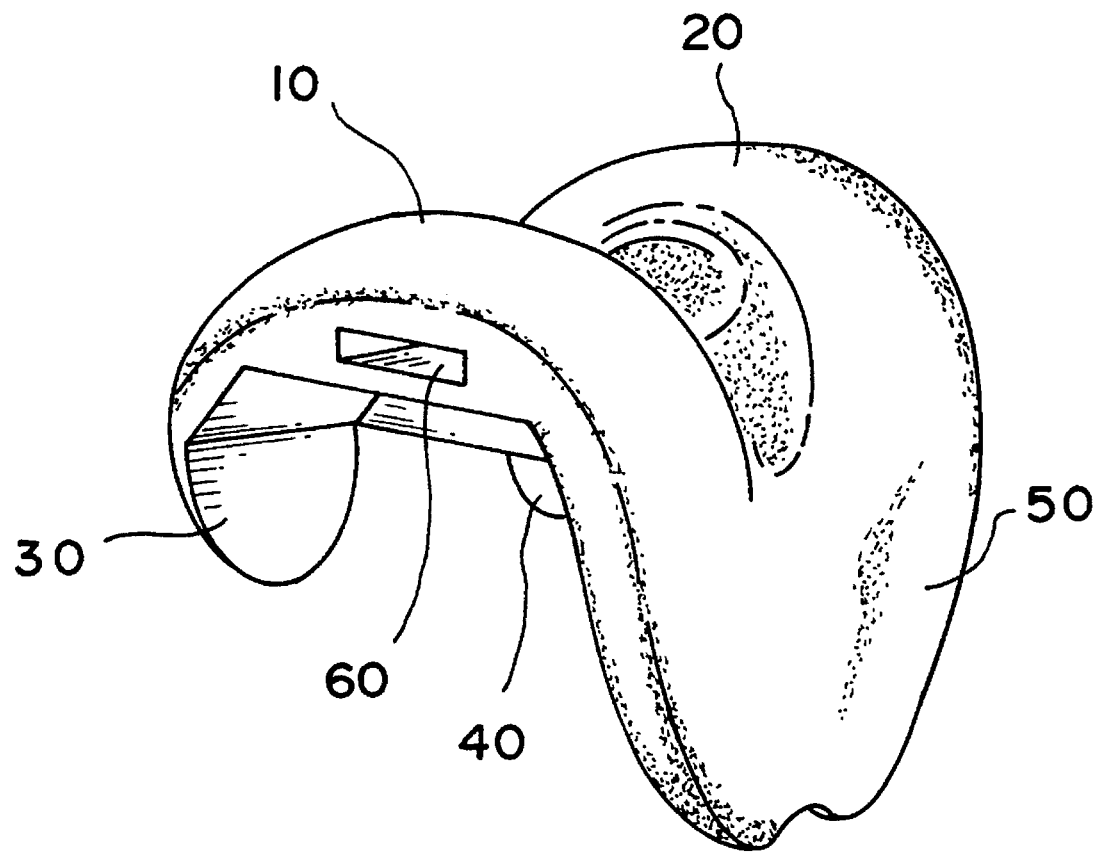
FIG. 1 shows a schematic view of a femoral component constructed in accordance with a first preferred embodiment of the present invention.

As shown in FIG. 1, a femoral component constructed in accordance with a preferred embodiment of the present invention comprises a lateral condyle protecting top 10, a medial condyle protecting top 20, a posterio femoral condyle protecting edge 30 of the lateral condyle protecting top 10, a posterio femoral condyle protecting edge 40 of the medial condyle protecting top 20, and a condyle groove protecting edge 50, which are all similar in construction to those of a femoral component used in the artificial knee joint of the prior art. In addition, the present invention is further provided with a retaining slot 60 located in the outer side of the lateral condyle protecting top 10. Similarly, the medial condyle protecting top 20 is provided with a retaining slot (not shown in the drawing) which is similar in shape and opposite in location to the retaining slot 60.

Figure 2:
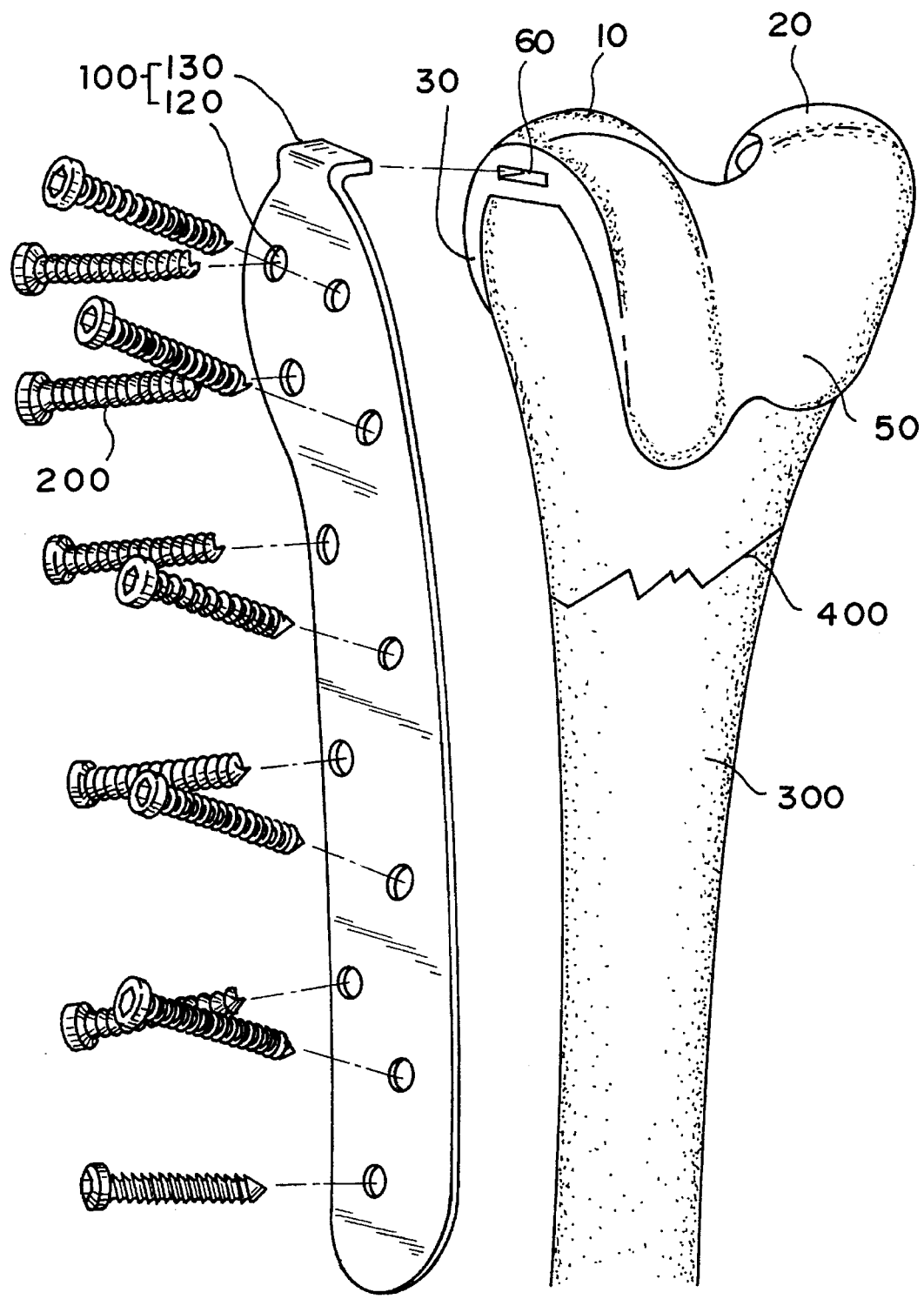
FIG. 2 is a schematic view showing the use of the femoral component in FIG. 1 in combination with a femoral hipbone rehabilitating bone plate.

The working of the femoral component of the present invention and a femoral hipbone rehabilitating bone plate 100 invented by the present inventors is schematically illustrated in FIG. 2 in which the reference numerals, such as 10, 20, 30, 50 and 60, are similar in definition to those of FIG. 1. The bone plate 100 is provided with a hooked coupling element 130 engageable with the retaining slot 60 of the present invention. The bone plate 100 is further provided with a plurality of threaded holes 120 dimensioned to hold therein securely a plurality of bone screws 200 which are to be fastened onto a femur 300 having a fracture 400.

Figure 3:
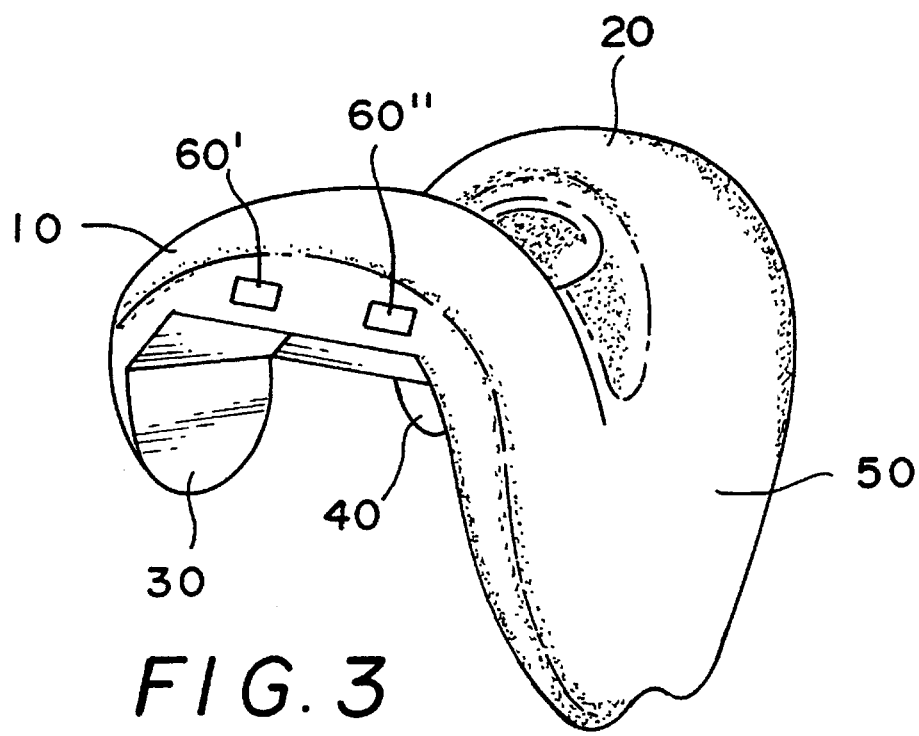
FIG. 3 shows a schematic view of a femoral component constructed in accordance with a second preferred embodiment of the present invention.

A femoral component constructed in accordance with a second embodiment of the present invention is illustrated in FIG. 3 in which the reference numerals, such as 10, 20, 30, 40 and 50, are similar in definition to those of FIG. 1. The lateral condyle protecting top 10 of the femoral component of the present invention is provided with two hooking slots 60' and 60" functioning as the retaining slot 60 of the femoral component in FIG. 1. The medial condyle protecting top 20 is similarly provided with two hooking slots (not shown in the drawing) which are similar in shape and opposite in location to the hooking slots 60' and 60" of the lateral condyle protecting top 10.

Figure 4:
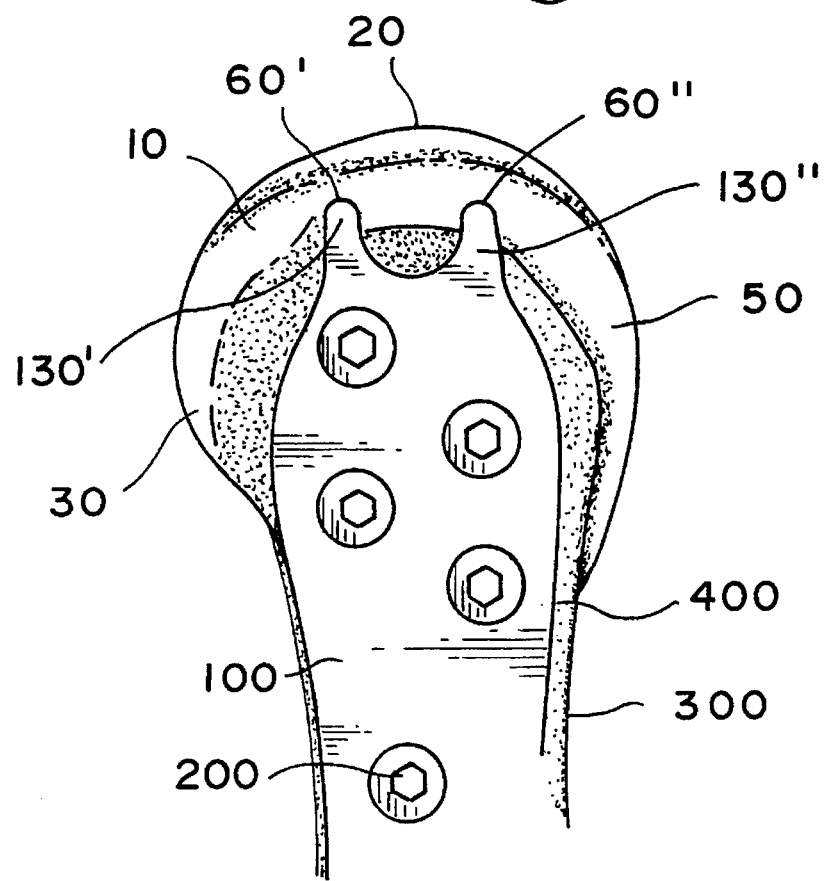
FIG. 4 is a schematic view showing the working of the femoral component in FIG. 3, which engage the coupling elements of the femoral hipbone rehabilitating bone plate.

The working of the femoral component shown in FIG. 3 in combination with the femoral hipbone rehabilitating device invented by the present inventors is shown schematically in FIG. 4 in which the reference numerals, such as 10, 20, 30, 50, 60' and 60", are similar in definition to those of FIG. 3, and in which the reference numerals, such as 100, 200, 300 and 400, are similar in definition to those of FIG. 2, and 130' and 130" are similar in definition to 130 in FIG. 2. As shown in FIG. 4, the hooked coupling elements 130 and 130' of the bone plate 100 engage respectively the hooking slots 60' and 60" of the present invention.

The embodiment of the present invention described above is to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. An implantable femoral component of an artificial knee joint comprising:

a lateral condyle top portion;

a medial condyle top portion;

a condyle groove edge portion integrally interconnecting said lateral condyle top portion and said medial condyle top portion; and means for coupling an elongated femoral bone rehabilitating plate adapted to be secured to a femur at a location spaced from the artificial knee joint to said femoral component, said coupling means including a pair of spaced retaining slots formed in one of said lateral and medial condyle top portions;

said implantable femoral component further comprising, in combination, an elongated femoral bone rehabilitating plate adapted to be secured to a femur at a location spaced from the artificial knee joint, said elongated femoral bone rehabilitating plate being provided with a coupling element attached to said coupling means.

2. The implantable femoral component of claim 1, wherein said coupling element in hook-shaped.

* * * * *